(12) United States Patent
Raether et al.

(10) Patent No.: US 6,369,165 B1
(45) Date of Patent: Apr. 9, 2002

(54) METHOD FOR THE PRODUCTION OF POLYMERS FROM N-VINYL COMPOUNDS

(75) Inventors: Roman Benedikt Raether, Ludwigshafen; Wolfgang Paulus, Mainz; Frank Braun, Niederkirchen; Klaus Müllen, Köln; Markus Klapper; Marco Steenbock, both of Mainz, all of (DE)

(73) Assignee: BASF Akiengesellschaft & Max-Planck-Gesellschaft (DE)

( * ) Notice: Subject to any disclaimer, the term of this patent is extended or adjusted under 35 U.S.C. 154(b) by 0 days.

(21) Appl. No.: 09/622,309

(22) PCT Filed: Feb. 11, 1999

(86) PCT No.: PCT/EP99/00891

§ 371 Date: Aug. 16, 2000

§ 102(e) Date: Aug. 16, 2000

(87) PCT Pub. No.: WO99/42501

PCT Pub. Date: Aug. 26, 1999

(30) Foreign Application Priority Data

Feb. 19, 1998 (DE) .......................................... 198 06 853

(51) Int. Cl.⁷ .......................... C08F 22/38; A01N 57/00
(52) U.S. Cl. ............................... 525/326.9; 525/328.2; 525/328.4; 525/330.5; 525/54.1; 526/264; 526/261; 514/91; 514/93
(58) Field of Search .................... 525/326.9, 328.2, 525/328.4, 330.5, 54.1; 526/264, 261; 514/91, 93

(56) References Cited

U.S. PATENT DOCUMENTS

| | | | |
|---|---|---|---|
| 4,581,429 A | 4/1986 | Solomon et al. | 526/220 |
| 5,322,912 A | 6/1994 | Georges et al. | 526/204 |
| 5,373,074 A | 12/1994 | Wu et al. | 526/218 |
| 5,444,135 A | 8/1995 | Cheradame et al. | 526/219 |
| 5,549,998 A | 8/1996 | Georges et al. | 430/109 |
| 5,629,394 A | 5/1997 | Cheradame et al. | 526/219 |

FOREIGN PATENT DOCUMENTS

DE    196 36 966    3/1998

OTHER PUBLICATIONS

Maryjaszewski et al. "Functional Polymers by Atom Transfer Radical Polymerization"Polym. Mater. Sci. Eng. vol. 76 (1997) pp. 147–148.

Abadie et al. "Synthese et Caracterisation de Coplymeres Sequences Par Transformation Du Centre Actif. Etude Des Passages Radicalaire–Cationique et Anionique–Radicalaire"Eur. Poly. J. vol. 26 (1990) pp. 515–520.

Hawker "Advances in 'Living' Free–radical Polymerization: Architectural and Structural Control" Trends in Polymer Sciences vol. 4 (1996) pp. 183–188.

Georges et al. "Taming the Free–radical Polymerization Process" Trends in Polymer Sciences vol. 2 (1994) pp. 66–72.

Turner et al. "Photoinitiated Block Copolymer Formation Via the "Living" Dithiocarbamate Free radical technique" Polym. Reprints vol. 29(2) (1988) pp. 6–7.

Lee et al. "Living Radical Polymerization of Vinyl Monomers Initiated by Aged "Cr²+BPO" in Homogenous Solution" Jnl. Chem. 6. vol. 74(7) (1978) pp. 1738–1749.

*Primary Examiner*—James J. Seidleck
*Assistant Examiner*—Olga Asinovsky
(74) *Attorney, Agent, or Firm*—Keil & Weinkauf

(57) ABSTRACT

A process for preparing polymers of N-vinyl compounds comprises polymerizing the vinyl compounds in the presence of free radicals of the formula I

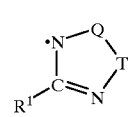
(I)

where Q is $NR^2$ or S and T is $CR^3R^4$ or S and $R^1$, $R^2$, $R^3$ and $R^4$ can be identical or different and are, independently of one another, hydrogen, $C_1$–$C_{20}$-alkyl or $C_6$–$C_{18}$-aryl.

9 Claims, No Drawings

METHOD FOR THE PRODUCTION OF POLYMERS FROM N-VINYL COMPOUNDS

The present invention relates to a process for preparing polymers of N-vinyl compounds. Furthermore, the present invention relates to the use of free radicals for preparing polymers of N-vinyl compounds. The present invention also relates to the polymers obtainable by the process of the present invention and also to their use.

A customary process for polymerizing N-vinyl compounds such as 1-vinyl-2-pyrrolidone (N-vinylpyrrolidone, hereinafter referred to as NVP) or N-vinylformamide (hereinafter referred to as NVF) is free-radical polymerization. It also allows the copolymerization of the N-vinyl compounds with other monomers. However, due to unavoidable secondary reactions such as chain transfer, disproportionation, recombination or elimination, the molecular weight distribution can be controled only with great difficulty. Normally, polymers having a polydispersity PD of 2.0 or more are obtained. PD is defined as PD $=M_w/M_n$, where $M_w$ is the weight average molecular weight and $M_n$ is the number average molecular weight. The architecture and structure of the polymers can also be influenced only with difficulty.

For these reasons, controled free-radical polymerization, sometimes also known as living radical polymerization, has been developed for preparing polymers having a narrow molecular weight distribution. This method is described, for example, in M. K. Georges et al., Trends in Polymer Science, Vol. 2, No. 2 (1994), pages 66 to 72. The basic strategy of this method is to block the reactive free-radical chain ends of the growing polymer chain periodically and then to reactivate them in a controled way (reinitiation). The dynamic equilibrium between active and dormant form leads to a small, static concentration of free polymer radicals.

EP-A 135 280 describes the use of stable N-oxyl radicals which combine reversibly with the reactive chain ends. However, this process does not give high molecular weight polymers, but only oligomers.

A particular group of initiators for controled free-radical polymerization are compounds which can be dissociated into free-radical initiators and N-oxyl radicals (Trends in Polymer Science, 4(6), 1996, 183–188). These compounds make it possible, for example, to produce branched polymers. However, only selected monomers can be polymerized and the reaction temperatures are unsatisfactorily high.

In general, the reaction rates in the polymerization of monomers in the presence of N-oxyl radicals are too low for many industrial purposes. For this reason, concomitant use has been made of, for example, strong organic acids (U.S. Pat. No. 5,322,912). However, these can cause difficulties in the work-up of the products.

DE-A 195 16 967 describes processes in which vinylic monomers are polymerized in the presence of customary free-radical initiators and electron donors which stabilise the free-radical chain end.

WO 94/18241 describes the polymerization of NVP using a plurality of initiators which have different decomposition temperatures. Such regulation is cumbersome and the polymers obtained are not terminated by functional groups which can be utilized for reinitiation.

In Polym. Mater. Sci. Eng., Vol. 76, pp. 147–148 (1997), Matyjaszewski describes the controled free-radical polymerization of NVP by atom transfer radical polymerization (ATRP). However, this ATRP method requires heavy metals. The reaction product poly-NVP is a good complexing agent for these heavy metals, which is why the poly-NVP prepared by ATRP contains heavy metals and is therefore unsuitable for use in medicine.

Polymers which have been free-radically polymerized using a regulator can be converted into block copolymers by reinitiation in the presence of a further monomer. In Eur. Polym. J., Vol. 26(5), pp. 515–520 (1990), Abadie discloses that block copolymers comprising NVP can, in principle, also be obtained by a change in the reaction mechanism. This process has the disadvantage that an additional process step is required compared to a purely free-radical method.

In Polym. Reprints (Am. Chem. Soc., Div. Polym. Chem.) (1988), Vol. 29(2), p. 6–7, Turner discloses the synthesis of a block copolymer comprising NVP and styrene, but the molar mass of the product is lower than that of the starting polymers.

In J. Chem. Coc. Faraday Trans. 1, Vol. 74(7), pp. 1738–1749 (1978), Munam Lee describes a controled free-radical polymerization of NVP. However, the polymerization proceeds very slowly: after a reaction time of 40 hours, only "traces" of polymer are found.

As regulators for free-radical polymerization, it is also possible to use triazolyl radicals, as taught by the earlier application DE-P 19636996.7, which is not a prior publication. The application nominates vinylaromatics, alkyl esters of acrylic acid and methacrylic acid, and acrylonitrile as preferred monomers. Homopolymers and random copolymers of N-vinyl compounds are not mentioned.

It is an object of the present invention to provide a novel process for preparing polymers comprising N-vinyl compounds such as NVP and NVF, which process does not have the abovementioned disadvantages. Furthermore, the new process should allow very good control over both the molecular weight distribution and the architecture and structure of the polymers. In addition, the process should have a sufficiently high reaction rate, even at relatively low temperatures. The polymers obtained should be free of heavy metals so that they can be used in medicine. The process should also make it possible to prepare block copolymers from blocks of N-vinyl compounds and blocks of other monomers in a simple manner without changing the reaction mechanism.

We have found that this object is achieved by a process for preparing polymers of N-vinyl compounds, in which process the N-vinyl compounds are polymerized in the presence of free radicals of the formula I

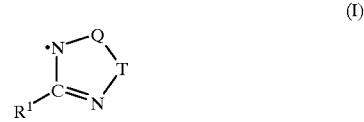

(I)

where Q is $NR^2$ or S and T is $CR^3R^4$ or S and $R^1$, $R^2$, $R^3$ and $R^4$ can be identical or different and are, independently of one another, hydrogen, $C_1$–$C_{20}$-alkyl or $C_6$–$C_{18}$-aryl. For the purposes of the present invention, the free radicals represented by the formula I also include their tautomers and positional isomers. The alkyl groups can be either linear, branched or cyclic. They can be either unsubstituted or substituted, for example by one or more halogen atoms such as chlorine, nitrile groups, $NO_2$, sulfonic acid groups, hydroxy groups, alkyl ester or aryl ester groups. Furthermore, the alkyl groups can contain sulfoxide or carbonyl groups. The alkyl groups include $C_1$–$C_{12}$-alkyl, preferably $C_1$–$C_{10}$-alkyl, for example methyl, ethyl, n-propyl, i-propyl, n-butyl, i-butyl, t-butyl, n-pentyl, cyclopentyl, n-hexyl or cyclohexyl. Among these, particular preference is given to methyl. The preferred aryl groups include phenyl, naphthyl and biphenyl. The aryl groups can either be substituted by one or more substituents or be unsubstituted. Possible substituents are alkyl groups, for example $C_1$–$C_{10}$-alkyl, preferably $C_1$–$C_6$-alkyl such as methyl, ethyl, n-propyl, i-propyl, n-butyl, i-butyl or t-butyl, or hydroxy groups or halogen atoms such as chlorine. Furthermore, the aryl groups can also be substituted by one or more halogen atoms such as chlorine, nitrile groups, $NO_2$, sulfonic acid groups, alkyl ester or aryl ester groups. Among the aryl groups, particular preference is given to phenyl.

Examples of suitable free radicals I are thiatianolyls of the formula

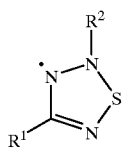

(I₁)

or dithiadianolyls of the formula

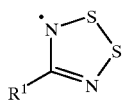

(I₂)

Preference is given to 2,5-dihydro-1H-1,2,4-triazol-2-yl free radicals (triazoyl radicals) of the formula

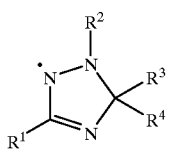

(I₃)

Particular preference is given to triazolyl radicals in which $R^3$ and $R^4$ are identical. In the very particularly preferred triazolyl radicals, $R^1$ is phenyl, $R^2$ is phenyl or methyl and $R^3$ and $R^4$ are each phenyl, biphenyl-2,2'-diyl, 6,6'-dimethylbiphenyl-2,2'-diyl or 5,5'-dimethylbiphenyl-2,2'-diyl.

2,5-Dihydro-1H-1,2,4-triazol-2-yl free radicals are known per se or are obtainable by methods known per se. Thus, the triazolyl free radicals are obtainable, for example, by irradiation of 1H-1,2,4-triazoles with y radiation or can be prepared by dehydrogenation of 4,5-dihydro-1H-1,2,4-triazoles using basic potassium hexacyanoferrate solution. Another method of obtaining triazolyl free radicals is the ring contraction of tetrazines in the presence of acids (Tetrahedron, 51 (47), 1995, 12883–12898).

Thiatrianolyls can be prepared, for example, by reduction of the corresponding thiatriazol-1-ium salts (J. Am. Chem. Soc. Perkin Trans 2 (1990) 1619). Dithiadianolyls are obtainable, for example, by reduction of the corresponding dithiadiazadium salts (Chem. Ber. 118 (1985) 3781).

The free radicals I can be generated in situ, for example by one of the abovementioned methods. Preference is given to preparing the free radicals I separately, isolating them and using them as such. Furthermore, in the process of the present invention, the free radicals I can also be used in the form of compounds II which can be dissociated into free-radical initiators and free radicals I. Such compounds can, for example, be summarized under the formula II

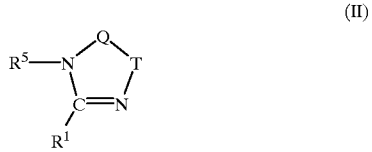

(II)

where $R^5$ is a group which, when split off, can initiate a free-radical reaction. In preferred compounds II, $R^5$ is alkyl, preferably $C_1$–$C_{10}$-alkyl; the alkyl group can be either linear or branched and can be substituted by one or more substituents, in particular halogen atoms such as chlorine or nitrile groups. The alkyl groups can also be interrupted by one or more heteroatoms such as oxygen. $R^5$ can also be an aryl group or a substituted aryl group, preferably $C_6$–$C_{18}$-aryl. Preferred groups $R^5$ are disintegration radicals of commercial free-radical initiators, e.g. isobutyronitrile or benzoyl.

The compounds II can be prepared, for example, by reaction of a free-radical source such as dibenzoyl peroxide or azobisisobutyronitrile with a free radical I. The free-radical source can here be dissociated into the disintegration radicals by methods known per se, for example thermally, photochemically or by a redox reaction.

The compounds II can be dissociated, for example, thermally or photochemically. The compounds II can also be dissociated by a redox reaction. In general, the compounds II are dissociated thermally. The compounds II generally dissociate at temperatures in the range from 0 to 300° C., preferably in the range from 50 to 150° C.

The process of the present invention can be carried out using one free radical I or one compound II. It is likewise possible to use different free radicals I or compounds II. Furthermore, it is also possible to use mixtures of free radicals I and compounds II.

The process of the present invention allows N-vinyl compounds to be converted into polymers. Preferred N-vinyl compounds are 1-vinyl-2-pyrrolidone (=N-vinylpyrrolidone, NVP) and N-vinylformamide (NVF). N-Vinylpyrrolidone is very particularly preferred.

If they are not used in the form of a compound II, the free radicals I are generally not capable of initiating a polymerization reaction. For this reason, according to a preferred embodiment, free-radical initiators can be used in addition. The free-radical initiators are known per se and described, for example, in Ullmanns Encyclopädie der technischen Chemie, 4th edition, Volume 15, page 187. Particularly suitable free-radical initiators are peroxides such as dibenzoyl peroxide and cumene hydroperoxide and, in particular, diazo compounds such as azobisisobutyronitrile (AIBN). It is also possible to use mixtures of various free-radicals initiators.

The molar amount of free-radical initiators can be from $10^{-6}$ to 1 mol/l, preferably from $10^{-4}$ to $10^{-1}$ mol/l, based on the volume of the monomers used. The molar ratio of free-radical initiators to free radical I is generally from 1:0.5 to 1:10, preferably from 1:0.5 to 1:5, in particular from 1:0.5 to 1:2.5.

According to a further preferred embodiment, use can also be made of electron donors as are described, for example, in DE-A 195 16 967. Preferred electron donors are phenothiazine derivatives or phenoselenazines of the formula

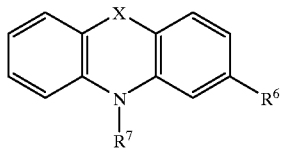

(III₁)

or

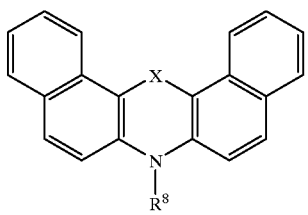

(III₂)

where

X is oxygen, sulfur or selenium, preferably sulfur, and $R^6$ is a hydrogen atom, —C₁—C₅-alkyl, preferably methyl or ethyl, —CF₃, halogen, preferably —Cl, —CN, alkyl sulfide, preferably $C_1$–$C_{10}$-alkyl sulfide, aryl sulfide, preferably phenyl sulfide, alkoxy, preferably $C_1$–$C_{10}$-alkoxy, aryloxy, preferably phenoxy, alkylamine, preferably $C_1$–$C_{10}$-alkylamine, dialkylamine, preferably di-$C_1$–$C_{10}$-alkylamine, arylamine, preferably phenylamine, diarylamine, preferably diphenylamine, $R^7$ is a hydrogen atom or –(Z)–Z¹, Z is an unbranched or branched $C_1$–$C_{25}$-alkylene group, preferably a $C_1$–$C_{25}$-alkylene group, particularly preferably a $C_1$–$C_{10}$-alkylene group, for example methylene, ethylene, 2-methylethylene, n-propylene or n-butylene, $Z^1$ is —OH, alkoxy, preferably $C_1$–$C_{10}$-alkoxy, aryloxy, preferably phenoxy, alkyl sulfide, preferably $C_1$–$C_{10}$-alkyl sulfide, aryl sulfide, preferably phenyl sulfide, —NH₂, alkylamine, preferably $C_1$–$C_{10}$-alkylamine, dialkylamine, preferably di-$C_1$–$C_{10}$-alkylamine, arylamine, preferably phenylamine, diarylamine, preferably diphenylamine, or $Z^2$, among which $Z^2$, —H₂, alkylamine or dialkylamine are preferred, $Z^2$ is a $C_4$–$C_7$-cycloaliphatic group, preferably a $C_5$–$C_6$-cycloaliphatic ring which can contain one or more —O—, —S— or —N(alkyl)— groups, preferably —N($C_1$–$C_{10}$-alkylamine)—, where the latter group is preferred and $Z^2$ is in each case linked to Z via a carbon atom and the groups —O—, —S— and —N(alkyl)— are not directly joined to one another.

The preferred phenothiazines include:

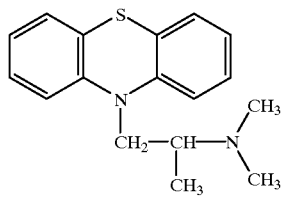

-continued

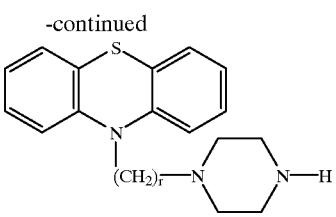

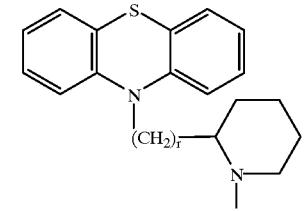

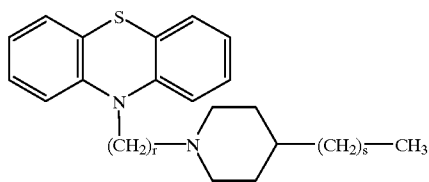

where r is in each case an integer from 2 to 11 and s is an integer from 1 to 4.

It is also possible to use mixtures of various electron donors.

The compounds used as electron donors are known per se or can be prepared by methods known per se and are described, for example, in J. H. Perlstein, Angew. Chem. Int. Ed. Engl. 16 (1977), pages 519 to 534 and M. R. Bryce, Aldrichimica Acta, Vol. 18 (1985), pages 73 to 77.

The molar ratio of electron donors to free radicals I can be in the range from 0.1:1 to 10:1, preferably from 0.5:1 to 2:1.

The molar ratio of electron donors to free-radical initiators can be in the range from 1:1 to 3:1, preferably from 1.6:1 to 2.4:1.

The process of the present invention can also be carried out in the presence of mixtures of the free radicals I and N-oxyl free radicals. Furthermore, it is possible for the process of the present invention to be carried out in the presence of mixtures of free radicals I, electron donors and N-oxyl free radicals. Here, the N-oxyl radicals serve as moderators, i.e. they reduce the reaction rate.

N-Oxyl free radicals are, as already indicated at the outset, known per se or they can be prepared by methods known per se. According to the invention, it is possible to use N-oxyl radicals having a wide variety of structures. These include both acyclic and cyclic N-oxyl radicals. In general, preference is given to cyclic N-oxyl radicals of the formula IV:

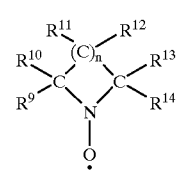

(IV)

In this formula, $R^9$ to $R^{14}$ can be identical or different and are, independently of one another, hydrogen, $C_1$–$C_{20}$-alkyl, $C_6$–$C_{18}$-aryl, —OH, —SH, —NH₂, alkylamine or dialkylamine. The variable n is an integer from 1 to 5, preferably 2 or 3. Among the alkyl groups, preference is given to $C_1$–$C_{10}$-alkyl, in particular $C_1$–$C_5$-alkyl; among the aryl groups, preference is given to phenyl. Preferably, $R^9$ and $R^{10}$ and also $R^{13}$ and $R^{14}$ are in each case phenyl or alkyl or one phenyl group and one alkyl group such as methyl or ethyl. $R^{11}$ and $R^{12}$ are preferably hydrogen. If n is greater than 1, the $CR^{11}R^{12}$ groups can be identical, but different $CR^{11}R^{12}$ groups can also be present. If more than one $CR^{11}R^{12}$ group is present, the radicals on these groups are preferably OH and hydrogen.

Preference is given to 2,2,6,6-tetramethyl-1-piperidinyloxy (TEMPO), 4-oxo-2,2,6,6-tetramethyl-1-piperidinyloxy (4-oxo-TEMPO), 4-hydroxy-2,2,6,6-tetramethyl-1-piperidinyloxy, 2,2,5,5-tetramethyl-1-pyrrolidinyloxy, 3-carboxy-2,2,5,5-tetramethyl-pyrrolidinyloxy and di-tert-butyl nitroxide. 2,6-Diphenyl-2,6-dimethyl-1-piperidinyloxy and 2,5-diphenyl-2,5-dimethyl-1-pyrrolidinyloxy can likewise be used. It is also possible to use mixtures of various N-oxyl radicals.

The molar ratio of N-oxyl free radicals to free radical I is generally in the range from 0.1:1 to 20:1, preferably in the range from 0.1:1 to 10:1, particularly preferably in the range from 0.1:1 to 2:1.

The molar ratio of the N-oxyl free radical to the free-radical initiator is preferably in the range from 0.5:1 to 5:1, in particular from 0.8:1 to 4:1, particularly preferably in the range from 1:1 to 1.5:1.

The polymerization according to the present invention can be carried out by a variety of methods, for example bulk, solution, emulsion or suspension polymerization. For example, the polymerization can be carried out in the melt, e.g. in an extruder or a kneader. Suitable solvents for solution polymerization are, for example, tetrahydrofuran, toluene, ethylbenzene or mixtures thereof.

The reaction conditions are generally not critical; the temperatures can be in the range from 0 to 220° C., preferably in the range from 20 to 180° C., and the reaction is usually carried out at atmospheric pressure although it is also possible to employ pressures of up to 30 bar. The reaction times are preferably selected by continuing the polymerization until the desired molecular weight is reached, for example from 1 hour to 6 days.

It can be advantageous to carry out the reaction under inert gas, for example nitrogen or a noble gas such as argon.

In the process of the present invention, the preferred procedure is to place the free-radical initiator and the free radical I or a compound II in the reaction vessel and to add the monomer or monomers and, if used, the solvent. However, it is also possible to employ the reverse order of addition. If additional use is made of electron donors or N-oxyl free radicals or mixtures thereof, they can be initially charged together with the free-radical initiators and the free radical I. They can, however, also be added separately or individually during the course of the polymerization reaction. The polymers can be worked up by precipitation, for example in methanol or hexane.

The molecular weights Mn (number average) of the polymers formed can vary within a wide range, for example from 5000 to 500,000 g/mol.

The process of the present invention can be used to prepare not only homopolymers but also random copolymers. Random copolymers are advantageously prepared by polymerizing the N-vinyl compounds together with suitable unsaturated monomers, in particular vinylic monomers.

Suitable vinylic comonomers are, in particular, olefins, vinyl chloride, vinylidene chloride, esters of vinyl alcohol and monocarboxylic acids having from 1 to 8 carbon atoms, e.g. vinyl acetate, vinylaromatics such as styrene, 2-vinylnaphthalene and 9-vinylanthracene, substituted vinylaromatics such as p-methylstyrene, α-methylstyrene, p-chlorostyrene, 2,4-dimethylstyrene and 4-vinylbiphenyl, $C_1$–$C_8$-alkyl esters of acrylic acid or methacrylic acid, in particular $C_1$–$C_4$ acrylates and $C_1$–$C_4$ methacrylates, unsaturated dicarboxylic acids, for example aliphatic unsaturated dicarboxylic acids such as maleic acid, fumaric acid and itaconic acid, or their derivatives such as anhydrides, esters and amides, in particular anhydrides such as maleic anhydride, or vinyl cyanides, in particular acrylonitrile. Mixtures of various comonomers can likewise be used.

Preferred comonomers are styrene, substituted styrenes, $C_1$–$C_4$ acrylates and $C_1$–$C_4$ methacrylates, in particular methyl methacrylate, and also acrylonitrile.

The proportion of comonomers is usually up to 80% by weight, preferably up to 50% by weight, particularly preferably up to 30% by weight, based on the resulting copolymer of N-vinyl compounds and comonomers.

Apart from the homopolymers and random copolymers described, the process of the present invention can also be used to prepare segmented copolymers such as block copolymers, star block copolymers, graft copolymers or graft block copolymers by reacting the polymers further, preferably without work-up, with other monomers or monomer mixtures having a different composition. It may here be necessary to add further amounts of free radicals I or compounds II, free-radical initiators, electron donors or N-oxyl free radicals or mixture thereof.

The process of the present invention also makes it possible to prepare block copolymers from
at least one polymer block A obtainable by polymerization in the presence of free radicals I and consisting of NVP homopolymer or NVP copolymer comprising up to 80% by weight, preferably up to 50% by weight, based on the block A, of comonomers and
at least one polymer block B obtainable by polymerization in the presence of free radicals I and comprising NVF homopolymer or NVF copolymer comprising up to 80% by weight, preferably up to 50% by weight, based on the block B, of comonomers,
where the polymer blocks A, B are joined to one another directly and not via structural units which are not part of the blocks.

Preferred comonomers for block A and B are the previously mentioned vinylic comonomers and also the monomers mentioned below for the block C.

If a polymer block of type A is designated by A and a polymer block of type B is denoted by B and groups derived from initiators and any moderators and terminators are ignored, then possible amphiphilic block copolymers according to the present invention are, for example: linear systems such as A-B, A-B-A, B-A-A, B-A-B, A-B-B or $(A-B)_n$, star-shaped systems such as $A(B)_n$, $B(A)_n$ or $(A)_n$-$B-A-(B)_m$, dendrimeric system such as $((A)_n-B)_mA$, $(((B)_n-A)_mB$, $(((A)_m-B)_nA)_pB$ or $(((B)_m-A)_nB)_pA$ or comb-like systems such as $((A)_n-A(B))_q$ or $((B)_n-B(A))_q$, where m, n and p are integers from 1 to 5 and q is an integer from 0 to 1000.

Furthermore, linear diblock and triblock copolymers are preferred according to the present invention. If the order of the letters A, B indicates the temporal order of the preparation of the blocks, block copolymers which are favorable according to the present invention can be represented schematically as A-B, B-A, B-A-B and A-B-A.

The process of the present invention also makes it possible to prepare isophilic block copolymers, i.e. block copolymers whose blocks consist of different monomers but have a comparable or at least similar solubility in the same solvent. According to the invention, these isophilic block copolymers comprise
- at least one polymer block A consisting of NVP homopolymer or copolymer, as has been defined above, and/or
- at least one polymer block B consisting of NVF homopolymer or copolymer, as has been defined above, and
- at least one polymer block C obtainable by polymerization in the presence of free radicals I of one or more hydrophilic monomers selected from the group consisting of acrylic acid, methacrylic acid, maleic acid, fumaric acid, itaconic acid, 2-acrylamido-2-methylpropanesulfonic acid, styrenesulfonic acid, the potassium, sodium and ammonium salts and also the amides of the abovementioned acids, $\omega$-hydroxy-$C_2$–$C_4$-alkyl acrylate, $\omega$-hydroxy-$C_2$–$C_4$-alkyl methacrylate, vinylimidazole, vinylcaprolactam, N-methylvinylimidazole, vinyl methyl ether and dimethylaminoethyl acrylate,
  where the polymer blocks of types A, B, C are joined to one another directly and not via structural units which are not part of the blocks.

Accordingly, the isophilic block copolymers always comprise the block C and further comprise either the block A or the block B, or comprise the blocks A, B and C.

If a polymer block of type A is denoted by A and a polymer block of type C is denoted by C and groups derived from initiators and any moderators and terminators are ignored, then possible amphiphilic block copolymers according to the present invention are, for example: linear systems such as A-C, A-C-A, C-A-A, C-A-C, A-C-C or $(A-C)_n$, star-shaped systems such as $A(C)_n$, $C(A)_n$ or $(A)_n$-C-A-$(C)_m$, dendrimeric systems such as $((A)_n$-C$)_m$A, $((C)_n$-A$)_m$C, $(((A)_m$-C$)_n$A$)_p$C or $(((C)_m$-A$)_n$C$)_p$A or comb-like systems such as $((A)_n$-A(C))$_q$ or $((C)_n$-C(A))$_q$, where m, n and p are integers from 1 to 5 and q is an integer from 0 to 1000.

Furthermore, linear diblock and triblock copolymers are preferred according to the present invention. If the order of the letters A, C indicates the temporal order of the preparation of the blocks, amphiphilic block copolymers which are favorable according to the present invention can be schematically represented as A-C, C-A, C-A-C and A-C-A.

The same block sequences also apply analogously to the blocks B and C: in the above schematic block sequences, A is replaced in each case by B.

The block C can be linked to the blocks A and B in any order, e.g. A-B-C, A-C-B, C-A-B, etc.

All abovementioned block copolymers comprising the blocks A and B, or A and C, or B and C, or A, B and C: the block copolymers of the present invention (the term block copolymers here refers to polymers whose molecules consist of preferably linearly linked blocks, where the blocks are joined directly to one another and where the term block refers to a section of a polymer molecule, which section comprises a plurality of monomer units which have at least one common feature which is not present in the directly adjoining sections) can be two-block copolymers, three-block copolymers or multiblock copolymers comprising more than three blocks. They are preferably uncrosslinked.

Block copolymers according to the present invention which are soluble in aqueous medium should also be taken to include those which are not directly soluble in the aqueous polymerization medium but which can be dissolved indirectly, e.g. by first dissolving them in a water-miscible organic solvent or in a mixture of water and such an organic solvent (e.g. in dioxane, tetrahydrofuran or their mixtures with water) and subsequently converting this solution (which, according to the present invention, can sometimes also be added directly to the aqueous polymerization medium) into an aqueous solution (in place of water, use is frequently also made of an aqueous solution of an acid and/or base), e.g. by means of dialysis or repeated addition of small amounts of water and subsequent distillative removal of the organic solvent used. Here, the term solution does not necessarily imply a molecular solution, but merely expresses the fact that a clear liquid is present and also encompasses micellar solutions, particularly also those which are not in thermodynamic equilibrium.

In the block copolymers of the present invention, the chain is generally terminated by a group which is derived from the free radicals I or from $R^5$. These groups can sometimes also have been replaced by a terminal oxyamine group. For various reasons, removal of the groups which are derived from the free radicals I can be desirable. In column 6, lines 54ff, U.S. Pat. No. 4,581,429 offers various possible methods of removing them. Methods which are of particular interest according to the present invention are those which lead to a hydrogen atom, a hydroxyl group or an ethylenically unsaturated terminal group.

The process of the present invention is, in particular, economical, since the reaction proceeds sufficiently quickly in the industrially interesting temperature range and the reaction rate can also be controled readily. The process of the present invention is largely insensitive to small amounts of moisture and it is also possible to convert mixtures of monomers into random copolymers.

The use according to the invention of the free radicals I or compounds II leads to polymers having reactive "living", free-radical chain ends, so that a block copolymer or another copolymer such as a star block copolymer, graft copolymer or graft block copolymer can be obtained simply by adding another free-radically polymerizable monomer (mixture) to the reactor. Isolation of the initially prepared polymer having a living chain end is not necessary, nor is the difficult and time-consuming "pole reversal" of the reactivity center, as is known from classical block copolymerization. Block copolymers or other copolymers comprising N-vinyl compounds can accordingly be prepared conveniently by the process of the present invention in a "single-vessel reaction". The process of the present invention also makes possible the simple preparation of block copolymers from monomers which cannot be polymerized anionically and/or cationically.

The resulting polymers of the N-vinyl compounds are free of heavy metals. The polymerized N-vinyl compounds and in particular the polyNVP homopolymer which is prepared by the process of the present invention are therefore particularly suitable for use in medicine. Adjustment of the polymerization conditions makes it possible to prepare, in particular, polyNVP having a molecular weight which enables it to pass through the human kidney. Such a polyNVP is therefore suitable as a blood plasma substitute.

EXAMPLES

Commercially available benzoyl peroxide was used without further purification. 2,5-Dihydro-1,3,5,5-tetraphenyl-1H-1,2,4, -triazol-2-yl was prepared by dehydrogenation of the corresponding 4,5-dihydro-1H-1,2,4-triazole using the method described in Tetrahedron 51(47), 12883–12898, 1995.

Comparative Experiment
Polymerization of NVP without free radical I 500 g of N-vinylpyrrolidone and 1 g of benzoyl peroxide as free-radical initiator were placed in a stirred reactor. After flushing with nitrogen gas, the mixture was heated to 130° C. while stirring and was held at this temperature for 5 hours. After cooling, the resulting polymer was precipitated by pouring the reaction mixture into cyclohexane and was dried.

The polyNVP obtained had a molecular weight (weight average) of 120,000 g/mol; the polydispersity PD weight average/number average was 8.4.

Experiment

The procedure of the Comparative Experiment was repeated, but 1.2 g of 1,3,5,5-tetraphenyl-2,5-dihydro-1H-1,2,4-triazol-2-yl (formula I3 where $R^1$ to $R^4$=phenyl) was placed in the reactor together with NVP and benzoyl peroxide.

The polyNVP obtained had a molecular weight (weight average) of 90 000, the polydispersity PD was 5.8.

The experiments showed that the additional use according to the present invention of the free radicals I leads to poly-N-vinyl compounds having a lower polydispersity and a lower molecular weight.

We claim:

1. A process for preparing a polymer of at least one N-vinyl compound, which comprises polymerizing the N-vinyl compound in the presence of at least one free radical of the formula I

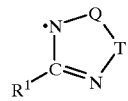

(I)

where Q is $NR^2$ or S and T is $CR^3R^4$ or S and $R^1$, $R^2$, $R^3$ and $R^4$ can be identical or different and are, independently of one another, hydrogen, $C_1$–$C_{20}$-alkyl or $C_6$–$C_{18}$-aryl.

2. A process as claimed in claim 1, wherein a free-radical initiator or an electron donor or a mixture thereof is also used.

3. A process as claimed in claim 1, wherein said at least one free radical I comprises a 2,5-dihydro-1H-1,2,4-triazolyl radical.

4. A process as claimed in claim 1, wherein said at least one free radical I is generated from at least one compound of the formula II

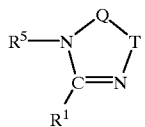

(II)

where $R^5$ is a group which, when split off, can initiate a free-radical reaction and Q, T and $R^1$ are as defined for formula I, which can be dissociated into a free-radical initiator and a free radical I.

5. A process as claimed in claim 1, wherein said at least one N-vinyl compound is 1-vinyl-2-pyrrolidone, (N-vinylpyrrolidone) or N-vinylformamide or a mixture thereof.

6. A polymer of at least one N-vinyl compound obtained by a process as claimed in claim 1.

7. A blood plasma substitute, comprising a polymer of at least one N-vinyl compound as claimed in claim 6.

8. A block copolymer containing at least one polymer block A obtained by polymerization in the presence of at least one free radical of the formula I

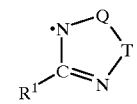

(I)

where Q is $NR^2$ or S and T is $CR^3R^4$ or S and $R^1$, $R^2$, $R^3$ and $R^4$ can be identical or different and are, independently of one another, hydrogen, $C_1$–$C_{20}$-alkyl or $C_6$–$C_{18}$-aryl and consisting of N-vinylpyrrolidone homopolymer or N-vinylpyrrolidone copolymer comprising up to 80% by weight, based on the block A, of comonomers and at least one polymer block B obtained by polymerization in the presence of at least one free radical I and consisting of N-vinylformamide homopolymer or N-vinylformamide copolymer comprising up to 80% by weight, based on the block B, of comonomers, which block copolymer has a linear structure selected from the group consisting of A-B, A-B-A, B-A-A, B-A-B, A-B-B or $(A-B)_n$, a star-shaped structure selected from the group consisting of $A(B)_n$, $B(A)_n$ or $(A)_n$-B-A-$(B)_m$, a dendrimeric structure selected from the group consisting of $((A)_n-B)_mA$, $((B)_n-A)_mB$, $(((A)_m-B)_nA)_pB$ or $(((B)_m-A)_nB)_pA$, or a comb-like structure consisting of $((A)_n-A(B))_q$ or $((B)_n-B(A))_q$, where m, n and p are integers from 1 to 5 and q is an integer from 0 to 1000.

9. A block copolymer obtained by reacting at least one polymer block A obtained by polymerization in the presence of a free radical of the formula I

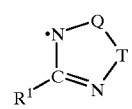

(I)

where Q is $NR^2$ or S and T is $CR^3R^4$ or S and $R^1$, $R^2$, $R^3$ and $R^4$ can be identical or different and are, independently of one another, hydrogen, $C_1$–$C_{20}$-alkyl or $C_6$–$C_{18}$-aryl and consisting of N-vinylpyrrolidone homopolymer or N-vinylpyrrolidone copolymer comprising up to 80% by weight, based on the block A, of comonomers and/or at least one polymer block B obtained by polymerization in the presence of at least one free radical I and consisting of N-vinylformamide homopolymer or N-vinylformamide copolymer comprising up to 80% by weight, based on the block B, of comonomers, and at least one polymer block C obtained by polymerization in the presence of at least one free radical of the formula I of one or more hydrophilic monomers selected from the group consisting of acrylic acid, methacrylic acid, maleic acid, fumaric acid, itaconic acid, 2-acrylamido-2-methylpropanesulfonic acid, styrenesulfonic acid, the potassium, sodium and ammonium salts, the amides of the abovementioned acids, ω-hydroxy-$C_2$–$C_4$-alkyl acrylate, ω-hydroxy-$C_2$–$C_4$-alkyl methacrylate, vinylimidazole, vinylcaprolactam, N-methylvinylimidazole, vinyl methyl ether and dimethylaminoethyl acrylate, and which block copolymers have a linear structure selected from the group consisting of A-C, A-C-A, C-A-A, C-A-C, A-C-C or $(A-C)_n$, a star-shaped structure selected from the group consisting of $A(C)_n$, $C(A)_n$ or $(A)_n$-C-A-$(C)_m$, a dendrimeric structure selected from the group consisting of $((A)_n$-$C)_m A$, $((C)_n$-$A)_m C$, $(((A)_m$-$C)_n A)_p C$ or $(((C)_m$-$A)_n C)_p A$ or a comb-like structure selected from the group consisting of $((A)_n$-$A(C))_q$ or $((C)_n$-$C(A))_q$, where m, n and p are integers from 1 to 5 and q is an integer from 0 to 1000.

* * * * *